United States Patent [19]

Chambers et al.

[11] Patent Number: 5,453,323
[45] Date of Patent: Sep. 26, 1995

[54] SUPERABSORBENT POLYMER HAVING IMPROVED ABSORBENCY PROPERTIES

[75] Inventors: Douglas R. Chambers; Hubert H. Fowler, Jr., both of Chesapeake, Va.; Yoji Fujiura; Fusayoshi Masuda, both of Kyoto, Japan

[73] Assignee: Hoechst Celanese Corporation, Somerville, N.J.

[21] Appl. No.: 74,282

[22] Filed: Jun. 9, 1993

Related U.S. Application Data

[63] Continuation of Ser. No. 753,737, Sep. 3, 1991, abandoned, which is a continuation-in-part of Ser. No. 685,974, Apr. 15, 1991, Pat. No. 5,145,906, which is a continuation of Ser. No. 413,760, Sep. 28, 1989, abandoned.

[51] Int. Cl.[6] .......................................... C08F 8/44
[52] U.S. Cl. ............... 428/402; 525/54.3; 525/54.31; 525/118; 525/119; 525/328.3; 525/328.9; 525/330.2; 525/369
[58] Field of Search .................. 525/118, 119, 525/328.9, 330.2, 54.3, 54.31, 369; 428/402

[56] References Cited

U.S. PATENT DOCUMENTS

| | | | |
|---|---|---|---|
| 4,497,930 | 2/1985 | Yamasaki et al. | 525/54.24 |
| 4,666,983 | 5/1987 | Tsubakimoto et al. | 525/119 |
| 4,683,274 | 7/1987 | Nakamura et al. | 526/216 |
| 4,794,166 | 12/1988 | Engelhardt et al. | 524/833 |
| 4,985,514 | 1/1991 | Kimura et al. | 526/88 |
| 5,032,628 | 7/1991 | Choi et al. | 523/409 |

*Primary Examiner*—Romulo H. Delmendo
*Attorney, Agent, or Firm*—Hugh C. Crall; Rosemary M. Miano

[57] ABSTRACT

Super-absorbent polymers having superior dryness properties when incorporated into absorbent articles are made from acrylic acid and crosslinking agent polymerized under controlled conditions.

14 Claims, No Drawings

SUPERABSORBENT POLYMER HAVING IMPROVED ABSORBENCY PROPERTIES

CROSS REFERENCE TO RELATED APPLICATIONS

This is a continuation of application Ser. No. 07/753,737 filed on Sep. 3, 1991 now abandoned. Which is a continuation-in-part of Ser. No. 07/685,974, filed Apr. 15, 1991 (now U.S. Pat. No. 5,145,906) which is a continuation of Ser. No. 07/413,760, filed Sep. 28, 1989 (now abandoned).

BACKGROUND OF THE INVENTION

The field of art to which this invention is directed is hydrogel-forming polymer compositions made from crosslinked polyacrylic acid.

Water-insoluble hydrogel-forming polymers which are capable of absorbing large quantities of water and aqueous fluid are well known compositions. Such polymers, which are known as superabsorbent polymers, are lightly crosslinked acid functional polymers which swell in water or aqueous fluids but do not dissolve in the fluids. Superabsorbent polymers have been found to be particularly useful in diapers, feminine hygiene articles and surgical dressings. Descriptions of superabsorbent polymers and their uses are found in U.S. Pat. Nos. 3,669,103 and 3,670,731.

U.S. Pat. No. 4,654,039 (Reissue 32,649) is directed to hydrogel forming polymer compositions which are described as substantially water-insoluble, slightly crosslinked, partially neutralized polymers, derived from unsaturated polymerizable, acid group-containing monomers and cross-linking agents. Such polymers are made by polymerizing the acid monomer and the crosslinking monomer in water using a redox initiator system, followed by partially neutralizing the acid groups with sodium hydroxide, then drying the polymer and pulverizing it to a powder.

British Patent No. 2,119,384 discloses superabsorbent polymers made by polymerizing in water acrylic acid in admixture with sodium acrylate and a crosslinking monomer using a persulfate initiator, followed by drying and then heating with a crosslinking agent having at least two functional groups capable of reacting with carboxyl groups.

In U.S. Pat. No. 4,497,930, superabsorbent polymers are made by polymerizing acrylic acid in an inverse emulsion process followed by crosslinking the polymer with a diepoxide compound.

According to U.S. Pat. No. 4,295,987, superabsorbent polymers are made by polymerizing acrylic acid and a multi-functional acrylate monomer in water using a persulfate initiator followed by neutralizing the acid groups with caustic and then blending in a divalent cation salt, e.g., zinc acetate, for additional crosslinking.

Numerous other patents disclose superabsorbent polymers and their uses, such as U.S. Pat. Nos. 4,076,663, 4,552,938, 4,507,438, 4,535,098, 4,820,773 and European Patent Application 189,163.

Many improvements have been made in the performance and properties of superabsorbent polymers over the years, such as in gel strength and absorbing capacity. However, such superabsorbent polymers do not have a balance of properties. Typically polymers with high elasticity modulus exhibit reduced absorbing capacity, which results, for example, in reduced diaper dryness. Polymers with increased absorbing capacity exhibit low absorbency under pressure and a reduced elasticity modulus which also reduces diaper dryness. European Patent Application 339,461 describes absorbent products made with superabsorbent polymers having the ability to swell against pressure.

There is a need for a superabsorbent polymer having a balance of properties which, when the polymer is used in a diaper, results in improved diaper dryness and leakage.

SUMMARY OF INVENTION

This invention is directed to superabsorbent polymers, i.e., hydrogel forming polymers. In one aspect, this invention pertains to an improved superabsorbent polymer composition. In another aspect, this invention pertains to articles made with superabsorbent polymers.

The superabsorbent polymer of this invention is made by forming an aqueous solution of acrylic acid, a crosslinking monomer which is a polyethylenically unsaturated polymerizable monomer and, optionally, a hydroxy containing polymer, adding to the aqueous solution a redox initiator system and, optionally, a thermal free radical initiator, allowing the temperature to rise to a peak temperature under adiabatic conditions, holding at the peak temperature to reduce the free monomer content to less than 1000 ppm, neutralizing 50 to 100 percent of the acid groups of the resulting polymer with a base, and optionally adding a multi-functional compound having at least two groups capable of forming covalent bonds with carboxylic acid groups, drying the polymer to a moisture content below about 10 weight percent, and pulverizing the dried polymer to a powder.

The superabsorbent polymer of this invention exhibits:

absorbency under pressure of 30 g/g minimum;

reabsorbing capacity of 40 g/g minimum;

elasticity modulus of $9.0 \times 10^4$ dynes/cm$^2$ minimum, recovery ratio of 85 percent minimum.

Articles made with the superabsorbent polymer of this invention exhibits dryness values of at least 40.

DESCRIPTION OF THE INVENTION

The primary monomer used to make the superabsorbent polymer of this invention is acrylic acid. The crosslinking monomer copolymerized with acrylic acid is a polyethylenically unsaturated polymerizable monomer having at least two polymerizable groups per molecule and which is soluble in water or in an acrylic acid-water solution. Examples of polymerizable groups are acrylic groups, methacrylic groups, allyl groups and vinyl groups. Crosslinking monomers include polyacrylic esters of polyols, polymethacrylic esters of polyols, polyallyl amines, polyallyl ethers, polyacrylamido compounds, polymethacrylamido compounds and divinyl-compounds. Specific examples of crosslinking monomers are tetrallyloxyethane, N,N'-methylene bisacrylamide, N,N'-methylene bismethacrylamide, triallylamine, trimethylol propane triacrylate, glycerol propoxy triacrylate, divinyl benzene and the like. Preferred crosslinking monomers are those which contain at least two allyl groups, most preferably four allyl groups. A most preferred monomer is tetraallyloxyethane.

Optional components used in making the superabsorbent polymers of this invention are water soluble hydroxy containing polymers, such as polysaccharides and vinyl or acrylic polymers. Examples of water soluble polysaccharides are starches, water soluble celluloses and polygalactomannans. Suitable starches include the natural starches, such as sweet potato starch, potato starch, wheat starch, corn starch, rice starch, tapioca starch and the like. Processed or modified starches, such as dialdehyde starch, alkyl-etherified starch, allyl-etherified starch, oxyalkylated starch, aminoethyl-etherified starch, and cyanoethyl-etherified starch are also suitable.

The water-soluble celluloses useful in this invention are those obtained from such sources as wood, stems, bast, seed fluffs and the like which are then derivatized to form hydroxyalkyl cellulose, carboxymethyl cellulose, methyl cellulose and the like.

Suitable polygalactomannans are guar gum and locust bean gums as well as the hydroxyalkyl, carboxyalkyl, and aminoalkyl derivatives.

Water soluble vinyl and acrylic polymers include polyvinyl alcohol and poly(hydroxyethyl acrylate).

The preferred polysaccharide for use in this invention is natural starch, such as wheat starch, corn starch and alpha starches.

In preparing the superabsorbent polymer of this invention, the acrylic acid and the water soluble polymer are reacted in the amount of about 90 to about 100 weight percent acrylic acid and 0 to about 10 weight percent water soluble polymer, said weight percents being based on the weights of acrylic acid and water soluble polymer. The amount of polyethylenically unsaturated crosslinking monomer will vary from about 0.005 to about 1.0 mole percent based on the moles of acrylic acid, and preferably about 0.01 to about 0.3 mole percent.

The polymerization initiators used in this invention are redox initiators and optionally thermal types. The redox initiators are used to initiate and to substantially complete the polymerization reaction. The thermal initiators if used are to ensure that the free monomer content of the product is reduced below 1000 ppm by weight.

Referring to the redox initiators, any of the well known water soluble reducing agents and oxidizing agents can be used in this invention. Examples of reducing agents include such compounds as ascorbic acid, alkali metal sulfites, alkali metal bisulfites, ammonium sulfite, ammonium bisulfite, alkali metal hydrogen sulfite, ammonium hydrogen sulfite, ferrous metal salts, e.g., ferrous sulfates, sugars, aldehydes, primary and secondary alcohols, and the like.

Oxidizing agents include such compounds as hydrogen peroxide, alkali metal persulfate, ammonium persulfate, alkylhydroperoxides, peresters, diacryl peroxides, silver salts, and the like. A particularly preferred redox initiator pair is ascorbic acid and hydrogen peroxide.

In order to obtain superabsorbent polymers having the superior properties as claimed in this invention, the reducing agent must be used in the amounts of about $2 \times 10^{-5}$ to about $2.0 \times 10^{-2}$ mole percent based on moles of acrylic acid. The amount of oxidizing agent used will vary from about $2.0 \times 10^{-3}$ to about 1.1 mole percent, based on moles of acrylic acid.

In order to ensure complete polymerization of the acrylic acid monomer and the crosslinking monomer, a thermal initiator can be included in the polymerization process. Useful thermal initiators are the "azo" initiators, i.e., compounds which contain the —N=N— structure. Any of the azo compounds which have some solubility in water or in an acrylic acid-water mixture and which have a 10 hour half life at 30° C. or above can be used. Example of useful azo initiators are 2,2'-azobis(amidino propane) dihydrochloride, 4,4'-azobis(cyanovaleric acid), 4,4'-butylazo-cyanovaleric acid, 2,2'-azobis(isobutyronitrile), and the like. A preferred azo initiator for use in this invention is 2,2'-azobis(amidinopropane) dihydrochloride. The thermal initiators are used in the amount of 0 to about 1 mole percent based on the weight of acrylic acid.

The polymerization process for preparing the compositions of this invention is conducted in water at a solids content, i.e., acrylic acid and water soluble polymer, of about 20 to about 30 weight percent, wherein the weight percent is based on the total weight of water, acrylic acid and water soluble polymer.

The process used to prepare the compositions of this invention is an adiabatic reaction which is initiated at a temperature of about 5° C. to about 20° C. and which causes a rise in temperature which does not exceed a peak temperature of about 90° C. Generally, the peak temperature will be about 60° C. to about 75° C. The time required to reach peak temperature will vary depending upon the concentration of monomers, the amount of initiator and the specific initiator used as well as the size of the reaction batch and whether or not the reactor is insulated. Generally, this time will be about 1 to about 2 hours. After the peak temperature is reached, the temperature is held within about 10° C. of the peak temperature, and preferably within about 5° C. for about 1 to about 12 hours to ensure that the polymerization is complete and that the residual monomer content is below 1000 ppm.

The carboxylic acid groups of the composition of this invention are then neutralized with a base in the amount of about 50 to about 100 mole percent, preferably about 65 to about 75 mole percent. The preferred bases are the alkali metal hydroxides with the most preferred base being sodium hydroxide. Other bases, such as alkaline earth metal hydroxides, ammonium hydroxide, alkali metal, alkaline earth metal and ammonium carbonates, bicarbonates, and alcoholates, amines and the like can also be used.

The post-crosslinking compound, which optionally is added to the reactants after the neutralization step, is any compound which has at least two reactive moieties which can react with or form a bond with carboxylic acid or carboxylic acid salt groups and which is somewhat water soluble. Organic compounds which contain epoxy groups, hydroxyl groups, amine groups, phenolic groups and halohydrin groups are suitable for such use.

Examples of useful post-crosslinking compounds are ethylene glycol diglycidyl ether, epichlorohydrin, glycerol, ethylene diamine, bisphenol A, and the like. The preferred post-crosslinking compound is ethylene glycol diglycidyl ether.

The post-crosslinking compound is added to the polymer in the amount of 0 to about 1.8 mole percent based on the moles of acrylic acid and preferably, when the crosslinking compound is a diglycidyl ether, in the amount of about 0.02 to about 0.15 mole percent.

As stated hereinbefore, the polymerization reaction is an adiabatic reaction conducted without the application of external heat. The monomers, i.e., acrylic acid, the crosslinking monomer and the polysaccharide if used are dissolved in water in the reactor. Dissolved oxygen is removed from the solution by a sparge of inert gas, e.g., nitrogen, and the temperature is lowered to about 5° C. to about 20° C. The polymerization initiators, i.e., the thermal initiator if used, the reducing agent and the oxidizing agent are added to the reactor with thorough mixing. After a short induction period, polymerization begins as indicated by a rise in temperature. Peak temperatures are reached in about 1 to 3 hours. Generally, the peak temperature will be about 60° C. to about 75° C. After the peak temperature is reached, the polymer is kept in a heat insulated container (which can be the reactor) for a time sufficient for the polymerization reaction to be completed as evidenced by the monomer content being reduced below 1000 ppm. Generally this time will be about 2 to about 12 hours.

When the polymerization reaction is complete, the polymer gel is removed and is chopped into small particles. An aqueous base is then added to neutralize some or all of the acid groups. The gel is again chopped to ensure uniform mixing of the base with the polymer. An aqueous solution of a post-crosslinking agent can then be added and the gel is again chopped to ensure uniform mixing. The gel is then heated at a temperature of about 20° C. to about 200° C. to effect reaction of the post-crosslinking agent with the carboxylic acid groups and dry the polymer to a moisture content of less than about 10 weight percent. The dried polymer is then ground and sieved to a particle size of about 20 to about 400 mesh U.S. Standard Sieve, with a preferred range of 20–200 mesh, and most preferably 95 percent of said particles are between 20 and 140 mesh.

In order to evaluate the polymer properties of the superabsorbent polymer, a model diaper is used. The diaper is constructed by placing a layer of pulp (14×37 cm) having a basis weight of 200 g/m² and a nonwoven backsheet. The superabsorbent polymer, 5 g, is then spread on the pulp layer as uniformly as possible. The polymer is then covered with a layer of pulp (14×37 cm) having a basis weight of 100 g/m² and a nonwoven top sheet.

The testing of the model diaper is conducted as follows:

1) 50 ml of a 0.9 weight percent aqueous saline solution are poured onto the center of the diaper at 5 minute intervals until a total of 150 ml of solution have been applied;

2) at 5 minutes and at 2 hours after the final addition of saline solution to the diaper, the dryness of the diaper is evaluated by 10 trained people who touch the diaper and each rate it from 1 to 5 at each time interval. The rating description is:

5—completely dry
4—slightly damp
3—damp
2—slightly wet
1—completely wet

3) The ratings by each person are added together for each time interval.

The lowest possible rating using the above described test is 10 and the highest is 50. The dryness rating for diapers using the superabsorbent polymers of this invention is at least 40.

The superabsorbent polymer of this invention is also evaluated by the following tests:

1) Absorbency Under Pressure

This test determines the ability of a superabsorbent polymer to absorb under a pressure of 20 g/cm² (i.e., child sitting down).

2) Reabsorbing Capacity

This test determines the ability of a superabsorbent polymer to absorb after it is partially hydrated (10 g/g saline concentration) and sheared a total of 50 times under a pressure of 22 g/cm² (i.e., slightly wet diaper being subjected to the stress or lying of sitting).

3) Elasticity Modulus

This test determines the ability of the superabsorbent polymer to retain its integrity when it is totally saturated to prevent structure collapse and loss of fluid (i.e., child sitting on wet diaper).

4) Recovery Ratio

This test determines the ability of the superabsorbent polymer to recover its shape after repeated applications of pressure.

Absorbency under Pressure is measured using an Automatic Absorbency Tester, Model KM 350 (Kyowa Seiko Co., Ltd.) and a plastic tube having an inner diameter of 25 mm and a length of 50 mm with a wire net (100 mesh) at the bottom of the tube. Samples having a mesh size of 32–100 are used in the test.

A test sample, 0.100 ±0.01 g, is placed in the plastic tube and is spread evenly over the wire net. A 100 g weight is placed on the sample. The plastic tube is placed in the center of the porous plate of the Tester under which is a reservoir containing saline solution (0.90 wt/vol. % NaCl aqueous solution). After 1 hour of absorption, the volume of absorbed saline solution is determined (a ml). A blank is run using the same procedure without the superabsorbent polymer (b ml). Absorbency under Pressure is equal to (a–b)×10.

Reabsorbing Capacity is determined as follows: a test sample, 1.00 g, is placed in a beaker containing 10.0 g of saline solution (0.9 wt/vol. % NaCl aqueous solution) and is left for 1 hour in order to obtain a uniform gel. The gel is then placed in a polyethylene bag which is sealed after removing the inside air. The bag containing the gel is placed on a press roller and is sheared under the following conditions:

Wt. of roller: 1 kg
Shearing speed by roller: 1 min./round
Rolling frequency: 50 times
Shear loading pressure: 22 g/cm²

The Reabsorbing Capacity of the gel is then determined on 1.10 g of the sheared gel placed in a plastic tube using the procedure described under Absorbency under Pressure, with exception that the 100 g weight is not used.

Elasticity Modulus is determined as follows: a test sample, 0.50 g, is placed in a beaker with 25.0 g of synthetic urine (aqueous solution of 0.8 weight percent NaCl, 2.0 weight percent urea, 0.08 weight percent Mg $SO_4 \cdot 7H_2O$, 0.03 weight percent $CaCl_2$, said weight percents being based on weight of solution) and is left for 1 to 3 hours in order to obtain a uniform gel. A portion of the gel, 0.2 g ±0.01 g, is then placed on a Creep Meter, Model RE 3305 (Yamaden Co., Ltd.) and the resistance to deformation is measured under a constant load of 15 g/cm².

The Elasticity Modulus in dynes/cm² is calculated from the ratio of the unit stress to the unit deformation.

The Recovery Ratio is determined using the Creep Meter and synthetic urine described for the Elasticity Modulus test. For the Recovery Ratio test, 0.3 g of the superabsorbent polymer are added to 15 g of synthetic urine in a plastic bottle. The bottle is capped, shaken and left for 1 hour so as to obtain a uniform gel. A portion of the gelled sample, 0.1 g, is placed on the Creep Meter and the elasticity of the gel is measured during 20 strikes of the table and sample with the transducer. The Recovery Ratio is calculated as the final height of polymer/initial height of polymer×100.

The following example describes the invention in detail. Part and percentages, unless otherwise designated, are parts and percentages by weight.

EXAMPLE

To an unheated/insulated reactor were added 800 parts of acrylic acid, 4.0 parts of tetraallyloxyethane, 300 parts of 8 percent oxidized starch in water and 2899.5 parts of water. Nitrogen was bubbled through the solution and the temperature was lowered to 10° C. When the dissolved oxygen was reduced below 1 ppm, the following initiators were added in the listed order:

0.8 part of 2,2-azobisamidino propane dihydrochloride in 10 parts of water;

0.008 part of ascorbic acid;

0.23 part of 35 percent hydrogen peroxide.

After an induction period of 20 minutes, polymerization began and a peak temperature of 60° C. was reached in two hours. The product gel was kept in the insulated reactor for an additional 2 hours, wherein the residual monomer was reduced below 1000 ppm.

To the polymer gel after being chopped in a meat grinder were added 644.38 parts of a 50 percent solution of sodium hydroxide in water. The temperature of the gel was about 60° C. before the caustic addition and the temperature of the caustic solution was 38° C. The gel was again chopped to mix in the basic solution for uniform neutralization. To the gel, which had exothermed to a temperature of 88° C.–93° C., were then added 0.8 part of ethylene glycol diglycidyl ether, the temperature of the solution being 24° C. The gel was again chopped three times to obtain uniform distribution of the post crosslinking agent. The polymer was then dried to a moisture content of 10 percent on a rotary type drum dryer heated with 100 psi steam. The resulting flake polymer was then ground and sieved to a particle size of 20–400 mesh (U.S. Standard Sieve).

The polymer exhibited the following properties:
Absorbency under pressure (AUP)—30 g/g
Reabsorbing capacity (Reab. Cap.)—42 g/g
Elasticity modulus (Elast. Mod.)—$9.3 \times 10_4$ dynes/cm$^2$
Recovery ratio—86%
Model diaper dryness
 5 minutes—43
 2 hours—43

Comparative Example

Polymers used in commercially available diapers were tested and compared with the polymer of this invention. The results of these tests are shown as follows:

| Polymer | Dryness 5 min. | Dryness 2 hrs. | AUP g/g | Reab. Cap. g/g | Elast. Mod. 104 dynes/cm$^2$ |
|---|---|---|---|---|---|
| Luvs Deluxe | 36 | 38 | 27 | 20 | 11.8 |
| Ultra Pampers Plus | 37 | 37 | 26 | 26 | 13.1 |
| Ultra Pampers | 34 | 36 | 23 | 28 | 9.9 |
| Snuggums Ultra | 34 | 38 | 24 | 29 | 8.4 |
| Regular Pampers | 31 | 33 | 25 | 23 | 12.7 |
| Huggies Supertrim | 31 | 35 | 21 | 31 | 7.8 |
| Thick Pampers Plus | 29 | 33 | 25 | 27 | 8.6 |
| SANWET ® IM-1500 | 30 | 38 | 12 | 38 | 7.4 |
| SANWET ® IM-1000 | 22 | 35 | 3 | 10 | 4.7 |
| Invention | 43 | 43 | 30 | 42 | 9.3 |

The superabsorbent polymers of this invention are useful in the manufacture of moisture absorbent articles, such as disposable diapers, sanitary napkins, incontinence garments, bandages, and the like. The superabsorbent compositions of this invention, due to the balance of properties described hereinabove, are particularly useful in the manufacture of thin and ultra thin disposable diapers which have excellent moisture absorbance capacity and reduced leakage.

In making absorbent articles with the compositions of this invention, the superabsorbent composition is mixed with or dispersed in a porous matrix of fibers. Such matrices are made from wood pulp or fluff, cotton liners, melt blown synthetic fibers or a mixture of the meltblown fibers and the wood fluff. The synthetic fibers can be polyethylene, polypropylene, polyesters, copolymers of polyesters and polyamides and the like.

Absorbent articles, such as disposable diapers, are made with a liquid-impermeable backing material, a liquid-permeable bodyside facing material and the liquid-absorbing composite sandwiched between the backing material and the facing material. The liquid-impermeable backing material can be made from commercially available polyolefin film and the liquid-permeable facing material can be made from a commercially available nonwoven material, such as spunbonded or corded fibrous web which is wettable and capable of passing urine.

The superabsorbent polymers of this invention can be used in the manufacture of absorbent articles such as those described in U.S. Pat. Nos. 3,669,103; 3,670,731; 4,654, 039; 4,699,823; 4,430,086; 4,973,325; 4,892,598; 4,798, 603; 4,500,315; 4,596,567; 4,676,784; 4,938,756; 4,537, 590; 4,935,022; 4,673,402; and European Patent Nos. 397, 110; 378,247 and 339,461, all of which are hereby incorporated by reference.

The capacity of articles made with fluff and superabsorbent polymers to absorb repeated doses of liquid is determined as follows:

1) An absorbent pad comprised of about 2 g absorbent polymer and about 12 g wood pulp is formed and compressed to a density of about 0.2 g/cm$^3$ and a diameter of about six inches.

2) Said absorbent pad is then dosed with 30 ml of 0.9 wt. % saline solution. After 20 minutes, 25 g. of 11 cm filter paper are placed on the pad with enough weight to have a force of 1 psi applied to the pad. The filter paper is then weighed. The pad is again dosed with 30 ml of the saline solution and after 25 minutes, fresh filter paper and weight are applied as described above, and the filter paper is weighed. The test is then repeated for the third time.

The rewet response is calculated as follows:

wet wt. of filter paper—dry wt of filter paper=rewet response

The rewet response of the superabsorbent polymer of this invention, Polymer A, and one having somewhat lower properties, Polymer B, as well as the properties of Polymers A and B are shown in the following tables.

TABLE 1

| Polymer | AUP | Reab. Cat. | Elast. Mod. | Rec. Ratio |
|---|---|---|---|---|
| A | 30 | 42 | $9.3 \times 10^4$ | 86% |
| B | 29 | 39 | $8.8 \times 10^4$ | 83% |

TABLE 2

| Wt. Fluff | Wt. Polymer | 1st Dose | 2nd Dose | 3rd Dose |
|---|---|---|---|---|
| \multicolumn{5}{c}{Rewet Response of Polymer A} | | | | |
| 9 | 0.8 | 0 | 11.3 | 22.5 |
| 6 | 1.6 | 0 | 5.2 | 16.9 |
| 12 | 1.6 | 0 | 4.6 | 11.1 |
| 9 | 2.4 | 0 | 3.3 | 8.0 |
| 6 | 3.2 | 0 | 1.9 | 3.6 |
| 12 | 3.2 | 0 | 3.6 | 4.8 |
| 9 | 4.0 | 0 | 2.8 | 4.6 |
| \multicolumn{5}{c}{Rewet Response of Polymer B} | | | | |
| 9 | 0.8 | 0 | 12.5 | 22.4 |
| 6 | 1.6 | 0 | 7.3 | 18.4 |
| 12 | 1.6 | 0 | 5.8 | 12.4 |
| 9 | 2.4 | 0 | 3.8 | 8.8 |
| 6 | 3.2 | 0 | 1.8 | 4.8 |
| 12 | 3.2 | 0 | 4.5 | 5.9 |
| 9 | 4.0. | 0 | 3.0 | 5.6 |

As can be seen, both superabsorbent polymers had 0 rewet response after one dose. After the second and third doses, however, the overall rewet response for articles made with the superabsorbent polymer of the invention was superior, i.e., lower, than that of articles made with the other polymer.

The principles, preferred embodiments and modes of operation of the present invention have been described in the foregoing specification. The invention which is intended to be protected herein, however, is not to be construed as limited to the particular forms disclosed, since these are to be regarded as illustrating rather than restrictive. Variations and changes may be made by those skilled in the art without departing from the spirit of the invention.

What is claimed is:

1. A superabsorbent polymer comprising a copolymer of acrylic acid, a multifunctional monomer and a water-soluble hydroxyl containing polymer wherein said superabsorbent polymer is obtained by aqueous solution polymerization and wherein the multifunctional monomer is soluble in the reaction mixture and contains at least 2 ethylenically unsaturated groups per molecule and is present in the amount of about 0.005 to about 1.0 mole percent based on the moles of acrylic acid and the water-soluble hydroxy containing polymer is present in the amount of 0 to about 10 weight percent based on the weight of acrylic acid, wherein said copolymer is neutralized with an aqueous base in the amount of about 50 to 100 percent of the carboxylic acid groups and is post-crosslinked with a multifunctional compound in the amount of 0 to about 1.8 mole percent based on the moles of acrylic acid, wherein said multifunctional compound contains at least two moieties which can react with or form a bond with carboxylic acid or carboxylic acid salt groups, wherein said superabsorbent polymer has an absorbency under Pressure of 30 g/g minimum, a Reabsorbing Capacity of 40 g/g minimum, an Elasticity Modulus of $9.0 \times 10^4$ dynes/cm$^2$ minimum, and a Recovery Ratio of 85 percent minimum.

2. The polymer of claim 1 wherein the ethylenically unsaturated groups of the multifunctional monomer are allyl groups.

3. The polymer of claim 2 wherein the multifunctional monomer is tetraallyloxyethane.

4. The polymer of claim 3 wherein the tetraallyloxyethane is present in the amount of about 0.01 to about 0.3 mole percent.

5. The polymer of claim 1 wherein said multifunctional monomer is selected from:

a) N,N'-methylene bisacrylamide b) trimethylol propane triacrylate c) glycerol propoxy triacrylate and d) divinyl benzene.

6. The polymer of claim 1 wherein the water soluble hydroxyl containing polymer is a polysaccharide.

7. The polymer of claim 6 wherein the polysaccharide is natural starch.

8. The polymer of claim 1 wherein said polymer has a particle size wherein 95% by weight of said particles are between 20–140 (U.S. Standard mesh).

9. The polymer of claim 1 wherein the post-crosslinking multifunctional compound is a polyglycidyl ether of a polyol.

10. The polymer of claim 9 wherein the polyglycidyl ether is the diglycidyl ether of diethylene glycol.

11. An absorbent article comprising a porous matrix of fiber having dispersed therein the polymer of claim 1.

12. An absorbent article according to claim 11 wherein said porous matrix is disposed between a liquid impermeable material and a liquid permeable material.

13. An absorbent article according to claim 11 wherein the absorbent polymer is present from 5–100% by weight based on said fiber.

14. A superabsorbent polymer comprising a lightly crosslinked acrylic acid polymer which swells in water or aqueous fluids but does not dissolve therein wherein said polymer is obtained by aqueous solution polymerization, wherein said polymer has the following properties: Reabsorbency Capacity of 40 g/g minimum; Elasticity Modulus of $9.0 \times 10^4$ dynes/cm$^2$ minimum; and Recovery Ratio of 85 percent minimum.

* * * * *